United States Patent [19]

Massó Remiro

[11] 4,121,582
[45] Oct. 24, 1978

[54] DIRECT BODY COVERING SHEET HAVING A CORRECTING AND/OR THERAPEUTIC ACTION

[76] Inventor: Jose Maria Massó Remiro, c/10 Granduxer, Barcelona, Spain

[21] Appl. No.: 745,924

[22] Filed: Nov. 29, 1976

[51] Int. Cl.² .............................................. A61F 13/00
[52] U.S. Cl. ..................................... 128/157; 128/402
[58] Field of Search ............... 128/157, 402; 2/243 R, 2/243 A, 2.1 R, 82

[56] References Cited

U.S. PATENT DOCUMENTS 3,070,476  12/1962  Miller ................................. 2/243 R

FOREIGN PATENT DOCUMENTS 2,357,821  6/1974  Fed. Rep. of Germany ........... 128/402

Primary Examiner—John D. Yasko
Attorney, Agent, or Firm—Wenderoth, Lind & Ponack

[57] ABSTRACT

A fabricated sheet structure includes a sheet of fabric which is flexible in all directions and which is corrugated so that opposite surfaces thereof are both provided with alternate recesses and ribs. One of the surfaces constitutes a mold for a layer of latex which has a ribbed inner surface which is fitted in the recesses of one surface of the sheet of fabric and which has a smooth outer surface.

3 Claims, 4 Drawing Figures

DIRECT BODY COVERING SHEET HAVING A CORRECTING AND/OR THERAPEUTIC ACTION

BACKGROUND AND SUMMARY OF THE INVENTION

The object of this invention is to provide a fabricated sheet structure from which garments, having a correcting and/or therapeutic action, are made.

The sheet structure is formed of a first sheet a fabric material which is flexible in all directions. The first sheet is corrugated so that both surfaces thereof are provided with alternate recesses and ribs. One of these surfaces constitutes a mold for a layer of latex material, one surface of which is complementary to the recesses and ribs of the sheet of fabric material and the other surface of which is smooth.

The latex sheet has a variable section, taken in the longitudinal direction of the ribs, such that the thickness of the latex sheet increases from one end of the ribs to the other, or vice versa.

The smooth surface of the latex layer has fixed thereto a second sheet of fabric material, preferably a smooth knitted fabric which is flexible in all directions.

The fabricated sheet structure may be formed into a tubular shaped body having a first narrowere end and a second wider end, with the latex layer increasing in thickness from the narrower end to the wider end, while the ribs are positioned inwardly of the tubular body and extend longitudinally with respect to the axis of the tubular body.

Also, the fabricated sheet structure may be in the form of a rectangular strip having a variable section with the ribs being arranged transversely of the strip.

The ribs formed by the first fabric sheet which constitutes the mold for the lates, are transversely deformable and constitute gripping ribs.

With the fabricated sheet structure thus constructed, a starting base is provided for producing garments having the following effects:
Thermotherapeutic
Hydrotherapic
Superficial
Electrophysiologic
Quinesiotherapic
Reanimating
Postural correction
Thermogenic The thermotherapeutic effect is produced due to the fact that the skin has a physiological hypothermy when compared with the internal temperature. Consequently, if the skin is covered with an impermeable material wherein there are virtual spaces, formed by the channels or recesses which are formed on one of the surfaces of the fabricated sheet structure of the invention, the thin layer of air which immediately surrounds the cutaneous surface, since it is in continuous contact and it remains stable for a long period of time, is heated and moistened. This enhances the gaseous interchange of carbonic anhydrids and oxygen, since the accumulated air will slowly flow towards the upper and lower parts, renewing but not cooling the internal parts.

For the above to take place, it is necessary for the channels or recesses of the garment, whether a girdle or a one-piece garment, to have been oriented to extend parallel to the longitudinal axis of the body covered by the garment.

The increase in temperature described is irradiated towards the internal medium, directly influencing the lowermost subcutaneous and muscular planes to indirectly increase the dermal capillar circulation, the permeability of which causes the substances dissolved in the blood plasma to pass to the tissues and to circulate between their cells.

The hydrotherapic effect is based on the increase in sweat secretion due to the thermal stimulus of heat, since the latex layer of the fabricated sheet structure is impermeable. Thus, there occurs a greater degree of elimination of water, electrolytes and metabolites, thereby beneficially acidifying the pH of the cutaneous layer.

The superficial effect is one of protection and is based on the epicutaneous emulsified layer composed of two non-miscible liquid phases. The water of the imperceptible perspiration and that of the sweat consitute an aqueous phase, while the lipids of the sebaceous secretion form the main ingredient of an oily phase.

When this emulsified layer is increased, the loss in cellular water is enhanced and there is formed a protecting layer which covers the cutaneous surface homogeneously in the same way as a cream, thus giving the skin a greater resistance, plasticity and smoothness.

The electrophysiologic effect is produced when the corneum layer has a high electrical resistance which can be diminished by a mechanical stimulus, such as a massage, thus beneficially increasing the epidermal permeability.

Due to the latex which is incorporated into the fabricates sheet structure from which the garments are made, and to its great elasticity, resistance and eacy recuperation, and as a result of the normal movements of the body of the user, a slight and smooth massage takes place on the anatomical zone covered by the garment, with a constant "massaging" of the subcutaneous and muscular planes. This favours the adipose micronization and, therefore, the elimination of the neutral fats through the vascular and lymphatic circulation, as well as a consumption of calories on the part of the muscular tissue which the fat reserve can use in the absence of gluicides, with the consequent decrease in adipose tissue. This produces a quinesiotherapic effect which facilitates an increase in the blood circulation which can produce a larger or better oxigenation of the tissues.

The reanimation effect is produced by physicochemical mechanisms, with the elimination of the toxic products formed during the cellular metabolism (muscular latic acid), and by the increase of the gaseous interchange (oxygen-carbonic anhydride), when influencing the dermal capillar circulation and the sweating and sebaceous external secretions.

Physical effects are produced when a slight pressure is exerted on the cutaneous surface and is transmitted to the internal medium, giving rise to a better support of organs situated in empty spaces and a better functioning thereof.

On the other hand, a psychic effect can be exerted on the person, when noticing the comfort of a garment having the aforementioned qualities. When an external stress is added thereto, it diminishes the stretching of the muscles, at the same time as it enhances their functional recovery, reducing the energetic waste and limiting the risk of possible fibrilla breakage.

The constitution of the sheet confers to the garment, according to its shape and formation, a correction action capable of eliminating alterations in the posture of the vertebral or articular column, thus preventing organic deficiencies and pathological postures, such as ciphosis, lardosi, scoliosis, as well as the effects of general indisposition, tiredness, fatigue, etc.

The thermogenic effect is produced in the same way as the therapeutic effect. However, its application is directed to the preservation of the temperature of an organism when in a strange ambient media.

This effect is exemplified by a diver who suffers from the negative thermal action of the water, at which time the diver consumes calories more rapidly than the human body can produce.

When the body is covered with an impermeable material wherein there are virtual spaces formed by the channels or recesses formed on the inner surface of the fabricated sheet structure of the invention, the thin layer of water surrounding the cutaneous surface heated, thus creating a microclima which retards the escape of calories. Thus, an increase in the dermal capillar circulation and a higher dynamic muscular efficiency are indirectly achieved.

In the majority of cases wherein an anatomical zone of a human being is covered, thus exerting a peripheric pressure, even as slight as possible, it is necessary for this pressure to be exerted equally over the entire covered zone. Therefore, the layer of latex is thicker at the widest part of the garment, and thinner at the narrowest part thereof.

The reason for this dimensional relationship is that when the covered surface is increased using the same elastic resistance, there results a pressure per unit of surface area which is proportionally lower than when this same elastic resistance is applied to a smaller surface. Therefore, an anatomically constructed garment, e.g. for a thigh, presses more tightly on the lower part of the thigh than on the upper part thereof.

When the thickness of the latex is increased, a variable is introduced into the elastic coefficient, proportionally increasing the pressure applied to the covered surface, so that the pressure per unit of surface in homogeneous at any point. This constitutes an important factor in the achievement of the aforementioned effects.

In special cases, such as for example in the treatment of varix and other circulatory problems, it is desirable to provoke a difference in pressures, the object of which is to stimulate the circulatory process.

In such situation, since the thickness of the latex is greater at one end of a molded tubular body, e.g. in the form of a stocking, by inverting the prior reasoning, that is to say by providing the narrowest portion or that having the smallest diameter with a greater thickness, a greater pressure, when exerted on the legs for example, is obtained on the heel than on the thigh. The applied pressure decreases towards the heart, thus stimulating the return or peripheral circulation.

BRIEF DESCRIPTION OF THE DRAWINGS

Other objects, features and advantages of the present invention will be described in detail below, with reference to that attached drawings, wherein.

DETAILED DESCRIPTION OF THE INVENTION

Figure 1:
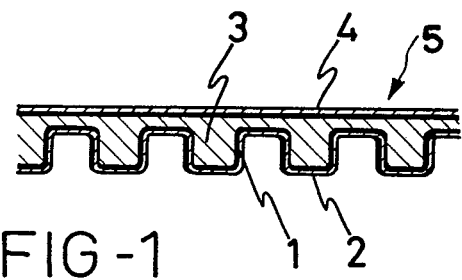
FIG. 1 illustrates a section of a fabricated sheet structure according to the invention.

As shown in FIG. 1 of the drawings, the fabricated sheet structure 5 of the present invention includes three basic elements. The first element is a first fabric sheet 1 which is flexible in all directions and which has a corrugated configuration such that first and second opposite surfaces of fabric sheet 1 are provided with alternate recesses and ribs.

The second element is a latex layer 3 which has a first relatively smooth surface and a second surface which has alternate ribs and recesses which are complementary to and in contiguous contact with the recesses and ribs, respectively, in one of the surfaces of the first fabric sheet 1.

The third element is a second fabric sheet 4 which is flexible in all directions and which has first and second opposite relatively smooth surfaces. On of the surfaces of the second fabric sheet 4 is fixed to the smooth surface of the latex layer 3.

Thus, the resultant fabricated sheet structure 5 has a first relatively smooth surface and a second ribbed surface which has ribs 2.

Figure 2:
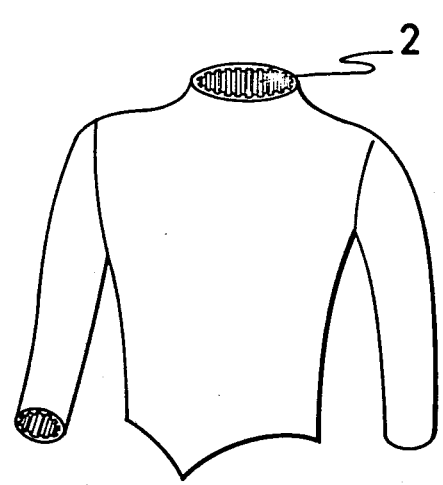
FIG. 2 is a perspective view of a garment formed according to the invention with the ribs oriented to extend parallel to the longitudinal axis of each part of the garment.

As shown in FIG. 2 of the drawings, the fabricated sheet structure may be formed into a garment, for example the illustrated garment covering the torso and arms. When this is done, the ribs 2 of the inner ribbed surface of the garment extend in a direction generally parallel to the longitudinal direction of the portion of the anatomy covered.

Figure 3:
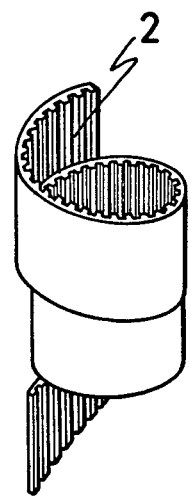
FIG. 3 is a perspective view illustrating the fabricated sheet structure in the shape of a rectangular strip (but wrapped to form a bandage), and showing the transverse orientation of the ribs.

Additionally, as is shown in FIG. 3 of the drawings, the fabricated sheet structure may be in the form of an elongated strip wherein the ribs 2 extend in a direction transverse to the longitudinal direction of the strip. Thus, the longitudinal strip may be wrapped around a part of the anatomy in the form of a bandage, as shown in FIG. 3 of the drawings.

Figure 4:
FIG. 4 is a partial longitudinal section showing the fabricated sheet structure in the shape of a tubular body, and illustrating how the latex layer varies in thickness, being thicker at the wider end than at the narrower end.

Even further, as shown in FIG. 4 of the drawings, which is a partial sectional view, the fabricated sheet structure of the present invention may be formed as a generally tubular body having a relatively wide first end and a relatively narrow second end. In this arrangement, as will be apparent from FIG. 4 of the drawings, the latex layer 3 preferably has a thickness which increases from the narrow end of the tubular body to the wider end of the tubular body.

Advantageously, both surfaces of the fabricated sheet structure 5 can be used, and although it is clear that its action is more energic when the ribbed surface is in contact with the skin, the use of the smooth surface is especially suitable in specific cases, such as for example when covering parts of the body affected by burns. It has been verified in practice that the use of girdles, wristlets, and even complete garments, depending on the affected areas, eliminates the normal itching of the skin and maintains the skin perfectly hydrated during the curing process.

On the other hand, due to the particular hydrothermic effects of the invention, research has been conducted on the use of the invention for psoriasis, a disease whose cause is unknown, whose evolution is chronic, and which is rebellious to all types of therapeutics used. More than 500 patients suffering from psoriasis were observed and controlled. These patients used different garments made in accordance with the described structure of the invention, and after a term of 2 weeks, using the garments for about 12 hours, a very remarkable reduction in the scales of the skin was seen. After 3 or 4 weeks a complete whitening in some patients was noted.

There is no doubt that the proposed garment can likewise be applied to other cutaneous pathological diseases, such as ichthyosis, which benefit from heat and from external cutaneous secretions.

The use of a garment according to the invention for cellulitis (a cutaneous disease characterized by a noninflammatory "pasting" of the sub-epidermic zones, with an increase in their thickness, reduction in their movement, a painful sensation and a granulous indured epidermic surface, such as an orange coloured skin), achieves an apparent improvement of the indured cells since, as is previously mentioned, the epicutaneous emulsified layer is increased. Thus, the epidermis achieves a higher elasticity, plasticity and smoothness. Due to the continuous micro-massage effect achieved according to the invention, and to the increase in the local temperature which irradiates heat towards the deep hypodermic planes, a micronization of the infiltrates and an acceleration of the interchanges between the cutaneous and the muscular surfaces can be produced due to the greater lymphatic and venous contribution, thus favouring re-absorption.

There is no doubt whatsoever, since this has been verified experimentally on a large number of persons, of the decrease produced by the adipose tissue, stored in excess in determined parts of the body prone to this accumulation of neutral fats (waist, abdomen and thighs). The action is mainly based on hydrothermal effects (loss of water due to the increase in the sebaceous-sweaty secretion due to the increase in local heat which causes better blood circulation and re-absorption of fatty substances) and on quinesiotherapeutic effects (constant and progressive micro-massage which potentializes the aforementioned effects and gives rise to the consumption of fats due to the increase of the muscular caloric needs, on being continuously and smoothly contracted).

Due to the continuous, smooth and flexible pressure characteristics, enhancing return circulation and preventing edema, it is believed that garments made according to the invention can be used for angiology for curing and preventing varix.

Various garments according to the invention can be used in orthopaedics for different parts of the body, since the resistance, flexibility and uniform pressure characteristics, in addition to the hydrothermal effects, of the garments are capable of achieving a high degree of postural correction, slowly and comfortably reducing the alterations and deformations of the vertebrae of joints.

This also applies to the working and athletic fields, both preventively, to avoid twists, sprains, torn ligaments, etc., since garments according to the invention increase the resistance of the elements which support the skeleton (muscles and ligaments), and potentialize the muscular contractibility and the flexiblity of the ligaments, enhancing an improved recovery after stretching, which calls for a lesser effort, a high yield and a lower injury index, as well as therapeutically, since the hydrothermal effect of garments according to the invention enhance the re-absorption of seroses of hematic extrabasations, produces an anti-inflammatory action (heat) and maintains a correct posture of the affected part. These facts are medically well known.

Also, a suitable garment having the above mentioned characteristics may be beneficial for pregnant women.

Garments according to the invention were used in four pregnancy cases (two during the sixth month of pregnancy, one during the seventh month of pregnancy, and one during the eighth month of pregnancy). Remarkable benefits were observed with respect to comfort, rest and less tiredness, and in one case, the condition of the abdominal cutaneous surface after pregnancy was improved, compared with others who had not used any garment of this type and on whom very apparent stretched striae appeared.

Recalling the mentioned properties of these garments, of having laminar flexiblity, of being capable of applying continuous, uniform pressure and of being perfectly adaptable to any surface, as well as the hydrothermal effect and the "supporting" effect on organs floating in "empty spaces" of the body, it will readily be understood why a pregnant woman maintains a more correct postural position of her vertebral column, and finds a supporting point and potentializes the resistance of her ligaments, which resistance tends to be strained by the heavy abdominal load, which is supported by the smooth and uniform pressure of the garment, without modifying the internal elements, nor affecting in the least the movements of the fetus. On the contrary, the garment on the invention helps the fetus in its normal adjustment during pregnancy and helps the abdominal muscle to maintain a functional tone, preventing abrupt expansion and exaggerated stretching of the cutaneous surface. Thus, breakage of the flexible dermic fibres in persons prone thereto as well as the formation of the anti-aesthetic "abdominal striae" produced in these cases by a mechanical effect of forced stretching, without the necessary time for a slow elongation with adaptation of the fibres of the corrective tissue to the new state, are avoided.

I claim:

1. A fabricated sheet structure for use in covering portions of the anatomy, said structure comprising:
   a first fabric sheet which is flexible in all directions, said first fabric sheet having a corrugated configuration such that first and second opposite surfaces thereof are provided with alternate recesses and ribs;
   a latex layer having a first relatively smooth surface and a second surface having therein alternate ribs and recesses which are complementary to and in contiguous contact with said recesses and ribs, respectively, in said first surface of said first fabric sheet;
   a second fabric sheet is flexible in all directions, said second fabric sheet having first and second opposite relatively smooth surfaces, said first surface of said second fabric sheet being fixed to said smooth surface of said latex layer; and
   said second surface of said second fabric sheet comprising a first, relatively smooth surface of said structure, and said second surface of said first fabric sheet comprising a second, ribbed surface of said structure.

2. A structure as claimed in claim 1, wherein said structure is in the form of a tubular body having a relatively wide first end and a relatively narrow second end, said ribbed surface forming the inner surface of said tubular body, said ribs extending longitudinally of said tubular body, and the thickness of said latex layer increasing from said narrow end to said wide end of said tubular body.

3. A structure as claimed in claim 1, wherein said structure is in the form of a rectangular strip, said ribs extending in a direction transverse to the longitudinal dimension of said strip.

* * * * *